United States Patent [19]

Babb et al.

[11] 4,336,881

[45] Jun. 29, 1982

[54] AQUEOUS ACID CONCENTRATE FOR HEMODIALYSIS DIALYSATE

[75] Inventors: Albert L. Babb; Belding H. Scribner, both of Seattle, Wash.

[73] Assignee: Diachem, Inc., Arlington Heights, Ill.

[21] Appl. No.: 132,866

[22] Filed: Mar. 24, 1980

Related U.S. Application Data

[63] Continuation-in-part of Ser. No. 48,757, Jun. 14, 1979, abandoned.

[51] Int. Cl.$^3$ .............................................. B65D 85/00
[52] U.S. Cl. ................................ 206/525; 210/321.3; 252/1; 252/364
[58] Field of Search ................ 210/321.3; 252/1, 364; 206/525

[56] References Cited

U.S. PATENT DOCUMENTS 4,202,760  5/1980  Storey et al. ..................... 210/321.3

OTHER PUBLICATIONS

Travenol Catalog, Dated 7/5/67, pp. K19 and K20.
Weast, R., (Editor), *Handbook of Chemistry and Physics*, 54th ed., Crc Press, Cleveland, 1974, pp. D-192 and D-204.

*Primary Examiner*—Richard A. Schwartz

[57] ABSTRACT

An aqueous acid concentrate in unit dosage form, suitable for use in compounding a hemodialysis dialysate, is disclosed. The concentrate contains water, chloride ion in a concentration of about 3.5 Molar to about 4.7 Molar, sodium ion in a concentration of about 1.9 Molar to about 2.7 Molar, and dextrose in a concentration of about 0 Molar to about 0.4 Molar. Additionally, the concentrate may contain acetate group in a concentration of up to about 0.525 Molar, calcium ion in a concentration of up to about 0.125 Molar, potassium ion in a concentration of up to about 0.14 Molar, and magnesium ion in a concentration of up to about 0.09 Molar.

8 Claims, No Drawings

AQUEOUS ACID CONCENTRATE FOR HEMODIALYSIS DIALYSATE

CROSS-REFERENCE TO RELATED APPLICATIONS

This application is a continuation-in-part of U.S. patent application Ser. No. 048,575, filed on June 14, 1979, now abandoned.

FIELD OF INVENTION

This invention relates to hemodialysis, and particularly to compositions for the preparation of a dialysate for use in processes wherein the blood of a patient is dialyzed over a semipermeable membrane opposite a dialysate that contains sodium bicarbonate.

BACKGROUND OF THE INVENTION

Dialysis processes for the treatment of patients with kidney malfunction are coming into wider and wider use as more and more dialysis equipment becomes available. Dialysis processes are literally life-saving processes, but sometimes produce adverse secondary effects, such as fatigue and nausea. To reduce the adverse side effects and for other reasons, experimental work on the parameters of the process is being carried out, including investigation to improve the composition of the dialysate liquid.

Dialysate liquids must contain an alkalizing salt. In the early days of dialysis development sodium bicarbonate was used as the alkalizing agent. However, because of shelf-life and stability problems, as well as problems encountered by precipitate formation when calcium and/or magnesium salts are also present in the dialysate, sodium acetate was substituted for sodium bicarbonate as an alkalizing agent more than fifteen years ago. Even today dialysis solutions usually contain sodium acetate as the alkalizing agent. Sodium acetate solutions are more easily maintained than sodium bicarbonate solutions in a state of sterility; sodium acetate metabolizes in the bloodstream to sodium bicarbonate.

However, with the increasing acceptance and use of large surface area dialysis equipment, see Babb et al., Trans. Amer. Soc. Artif. Int. Organs XVII:81-91 (1971), evidence is accumulating that sodium acetate dialysates are not without shortcomings.

Additionally, it has been observed that patients dialyzed on large surface area dialyzers using a sodium acetate dialysate were rapidly depleted of bicarbonate ion during dialysis, thereby placing the patients in acidosis. Moreover, inasmuch as the influx rate of acetate ions into the patient's bloodstream during dialysis on a large surface area dialyzer usually is greater than the rate of metabolism of acetate ions to bicarbonate ions, a relatively large concentration of bicarbonate ions is generated after dialysis, producing alkalosis. Kirkendol et al., Trans. Am. Soc. Artif. Intern. Organs XXIII:3-99-403 (1977), recognized the drawbacks of sodium acetate dialysates as well as the impracticability of of sodium bicarbonate dialysates and investigated other potential substitutes for sodium acetate.

Graefe et al., in an article entitled "Less Dialysis-Induced Morbidity and Vascular Instability with Bicarbonate in Dialyzate," published in Annals of Internal Medicine 88:332-336, 1978, disclose that sodium bicarbonate-containing dialysate fluid produces less nausea, headache, vomiting, post-dialysis fatigue, hypo-tension, disorientation and dizziness than sodium acetate-containing fluid when used in a high-efficiently large-surface-area dialyzer.

A beneficial effect of sodium bicarbonate-containing dialysates in reducing incidence of atherosclerosis is recognized in Kluge et al., Int. Soc. Art. Org. 3A, p. 23 (April 1979).

These articles would suggest that sodium bicarbonate, rather than sodium acetate should be the alkalizer of choice in dialysate liquids. However, as pointed out hereinabove, sodium bicarbonate solutions present practical problems because these solutions are not bacteriostatic and thus may present sterility problems.

Aqueous sodium bicarbonate solutions, unlike aqueous sodium acetate solutions, are not self-sterilizing and cannot be prepared in advance of their use for dialysis. Common infectious organisms can survive and proliferate in sodium bicarbonate solutions; and infection of the patient is thus possible when there is even a minor and inadvertent departure from sterile technique in the handling of the dialysis process.

SUMMARY OF THE INVENTION

The aforementioned difficulties encountered with sodium bicarbonate dialysates can be resolved by generating bicarbonate ions on demand from two bacteriostatic, stable aqueous solutions. In particular, sodium bicarbonate as the alkalizing medium is generated in situ prior to passage of the dialysate solution over the dialysis membrane surface by the interaction of a stream of an aqueous solution containing dissolved sodium carbonate and a stream of an aqueous solution containing a dissolved acid of the group consisting of hydrochloric acid (HCl), acetic acid (HAc) and mixtures thereof to provide a dialysate having a pH of about 7.1 to about 7.4.

The aqueous sodium carbonate solutions are not bacteriostatic at all concentrations. In particular, aqueous sodium carbonate solutions having a sodium carbonate concentration of less than about 20 grams per liter of solution (calculated as anhydrous $Na_2CO_3$ concentration) are capable of supporting bacterial growth. Such dilute aqueous sodium carbonate solutions can be used to generate sodium bicarbonate in situ when freshly prepared; however, these dilute solutions are not suitable for extended storage and shipment from a manufacturing facility to the intended end use station. However, aqueous sodium carbonate solutions containing sodium carbonate in a concentration of about 20 grams or more per liter of solution are bacteriostatic. The aqueous acid solutions, on the other hand, are inherently bacteriostatic at all practical concentrations.

The present invention contemplates a concentrated aqueous hydrochloric acid solution that is eminently suitable for the compounding of a hemodialysis dialysate. The aqueous acid concentrate has a pH value of about 1 to about 2.5 and contains water, chloride ion in a concentration of about 3.5 Molar to about 4.7 Molar, sodium ion in a concentration of about 1.9 Molar to about 2.7 Molar, acetate group in a concentration of 0 Molar to about 0.525 Molar, potassium ion in a concentration of 0 Molar to about 0.14 Molar, calcium ion in a concentration of 0 Molar to about 0.125 Molar, magnesium ion in a concentration of 0 Molar to about 0.09 Molar, and dextrose in a concentration of 0 Molar to about 0.4 Molar.

Preferably, the aqueous acid concentrate is in the form of physically discrete units suitable as unitary dosages for each dialysis session, each unit containing a predetermined quantity of the various constituents calculated to produce the desired therapeutic effect when combined with an aqueous carbonate solution and diluted to produce a hemodialysis dialysate. Preferred unit dosage forms are sealed unit dose containers, more preferably sealed, collapsible unit dose containers, containing about 4 to about 20 liters of the aqueous acid concentrate.

DETAILED DESCRIPTION OF THE INVENTION

To prepare a dialysate, the concentrated sodium carbonate solution is first diluted with water, preferably deionized or tempered water, to provide a carbonate ion concentration that is sufficiently low to avoid the precipitation of any cations that may be present as additional constituents in the aqueous acid concentrate solution and that can form insoluble carbonates. The bacteriostatic, concentrated sodium carbonate solution can contain sodium carbonate in an amount of about 20 grams per liter of solution up to about 150 grams per liter of solution, and preferably about 105 to about 115 grams per liter solution, thus prior to use the concentrated sodium carbonate solution should be diluted sufficiently to avoid the formation of undesirable precipitates when the aqueous acid concentrate is combined therewith.

Presently known dialysis equipment can be used in conjunction with a dialysate compounded using the aforementioned bacteriostatic solutions. Prolonged existence of sodium bicarbonate in the dialysate liquid prior to use is avoided; instead, sodium bicarbonate is generated in situ in a desired concentration shortly before the dialysate liquid contacts the dialysis membrane.

The formulation of sodium bicarbonate by the reaction of sodium carbonate with hydrochloric acid or acetic acid is a well known chemical reaction which proceeds by the following equations:

$$Na_2CO_3 + HCl \rightarrow NaCl + NaHCO_3$$

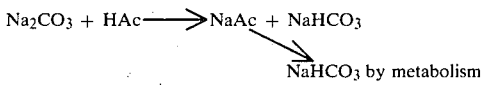

$$Na_2CO_3 + HAc \rightarrow NaAc + NaHCO_3$$
$$\searrow NaHCO_3 \text{ by metabolism}$$

The proportioning systems available on present dialysis equipment vary, thus the dilution ratios for each of the concentrates that are to be combined to form the ultimate dialysate may be different. However, in all instances the produced bicarbonate-containing dialysate has a pH in the range of about 7.1 to about 7.4 and an osmolality of about 200 to about 280 milliosmoles.

Since sodium bicarbonate is the preferred alkalizing material for minimizing side effects during hemodialysis, the preferred acid solution for producing the dialysate is a hydrochloric acid solution which produces no sodium acetate. However, from the aforementioned chemical reactions it can be seen that acetic acid produces equimolar amounts of sodium bicarbonate and sodium acetate; and acetic and hydrochloric acid mixtures produce even less sodium acetate. Such solutions are therefore preferable to the sodium acetate-alkalized dialysate solutions now used inasmuch as the major portion of the bicarbonate ion is derived from the reaction of sodium carbonate with hydrochloric acid but the total concentration of bicarbonate ion in the patient's bloodstream can be readily adjusted by the addition of minor amounts of acetate ion to the dialysate while the total concentration of acetate ion in the dialysate is minimized.

The use of a small amount of acetic acid in combination with hydrochloric acid is also helpful when using a standardized bacteriostatic sodium carbonate stock solution. That is, in a standardized system for the dialysis of patients some of whom may require different levels of sodium bicarbonate, it may be advantageous to make up a standard sodium carbonate solution, which, after suitable dilution and reaction with hydrochloric acid, will produce the desired amount of sodium bicarbonate for the patients who have the minimum level requirement for bicarbonate ions. For patients with bicarbonate ion requirements above the minimum, the necessary difference in bicarbonate ion requirement can then be readily supplied by substituting acetic acid for part of the hydrochloric acid while using the same standard sodium carbonate solution. The additional bicarbonate production from the same level of sodium carbonate is possible because acetic acid can produce two bicarbonate ions from each molecule of sodium carbonate (one immediately and the other through metabolic action in the bloodstream) while hydrochloric acid produces only one.

For example, a minimum alkalizing level of 35 milliequivalents (mEq) per liter of sodium bicarbonate may be taken as standard; and a level of sodium carbonate in a standard solution may be selected to produce 35 milliequivalents of sodium bicarbonate ion per liter when the sodium carbonate is diluted and then reacted with hydrochloric acid. For patients requiring minimum sodium bicarbonate levels the standard sodium carbonate solution would be reacted with an aqueous acid solution containing only hydrochloric acid.

For other patients who might require 40 milliequivalents of sodium bicarbonate per liter, for example, the additional five milliequivalents may be obtained from the same standard sodium carbonate solution by substituting acetic acid for the hydrochloric acid equivalent of five milliequivalents per liter. The substituted acetic acid will react with the sodium carbonate not only to produce immediately the same amount of sodium bicarbonate as the hydrochloric acid that it replaces (5 milliequivalents per liter) but it will also produce 5 milliequivalents per liter of sodium acetate which converts in the body to sodium bicarbonate. Thus, partial substitution of acetic acid for hydrochloric acid in a reaction with a standard minimum sodium carbonate solution increases the ultimate level of sodium bicarbonate to the extent of such substitution on a mol for mol basis. Alternatively, the addition of acetic acid can be dispensed with by increasing the amounts of hydrochloric acid and sodium carbonate that are reacted.

The amounts of other constituents of the dialysate fluid desired for proper electrolyte balance, e.g., NaCl, KCl, $CaCl_2$, $MgCl_2$, etc. are based on clinical requirements. These salts may be dissolved in the concentrated acid-containing solution, or may be supplied as a third solution, as desired. The former approach is preferred.

The aqueous acid concentrate solutions within the purview of the present invention can be prepared by dissolving the solid salts in water, preferably deionized or tempered water, and adding hydrochloric acid. The relative amounts of constituents are selected so as to provide in the concentrated solution a chloride ion concentration of about 3.5 to about 4.7 Molar, sodium ion concentration of about 1.9 to about 2.7 Molar, and a pH value of about 1 to about 2.5. Preferably, the pH value of the aqueous acid concentrate is about 1.8 to about 2.0.

Additionally, the aqueous acid concentrate can contain the acetate group in a concentration up to about 0.525 Molar, preferably in a concentration of about 0.15 Molar to about 0.35 Molar. Since aqueous solutions of acetate group-containing compounds contain ionized as well as unionized forms thereof, the term "acetate group" as used herein and in the appended claims includes both such forms.

Optionally, the aqueous acid concentrate can also contain potassium ion in a concentration up to about 0.14 Molar, calcium ion in a concentration up to about 0.125 Molar, and magnesium ion in a concentration up to about 0.09 Molar. Dextrose can be present in a concentration of about 0 to about 0.4 Molar, preferably in a concentration of about 0.2 to about 0.35 Molar.

The dialysate is provided to the membrane through a proportioning apparatus into which the respective constituent liquids are directed as separate streams at controlled rates, namely (1) a bacteriostatic stock sodium carbonate concentrate, (2) a bacteriostatic acid concentrate containing the remaining dialysate solute constituents, and (3) water, e.g., tempered or deionized water. Preferably, the sodium carbonate concentrate and the water are first combined; and the diluted sodium carbonate solution thus obtained is then combined with the acid concentrate to obtain a dialysate having a pH of about 7.1 to about 7.4. However, if desired the acid concentrate may also be diluted to a predetermined concentration before the bicarbonate is generated. The dilution ratios in any given instance will depend on the type of dialysis equipment that is used and the type of liquid proportioning means that is available.

The relative proportions and flow rates of the three liquid streams may be calculated and controlled by a suitable computer or microprocessor device; and the operation of the system may be monitored by a continuous reading of either the conductivity or the pH value of the final composite stream to the dialysis unit. Preferably both the conductivity and the pH of the obtained dialysate are monitored.

It has been determined that a sodium bicarbonate level of 35 milliequivalents per liter usually is suitable for patients having a minimal alkalizing requirement in their dialysate fluid. To obtain this level of sodium bicarbonate in the final dialysate solution (after reaction with hydrochloric acid and dilution), a standard, bacteriostatic concentrated sodium carbonate solution is prepared containing 1891 grams of sodium carbonate in a 4.5 U.S. gallon batch, i.e., containing 111 grams of sodium carbonate per liter of formed solution (calculated as anhydrous solute concentration), which is then further diluted with tempered water in a water-to-concentrate volume ratio of about 28 to 1 prior to use.

Suitable levels of hydrochloric acid and acetic acid in the acid-containing solution for patients requiring different levels of alkalizing bicarbonate are shown in the following Table.

| HCO$_3$ ions Required mEg/l | HCl (11.6N) ml/l | HAc (17.4N) ml/l |
|---|---|---|
| 30 | 90.6 | 0 |
| 35 | 105.7 | 0 |
| 40 | 90.6 | 10.05 |
| 45 | 75.5 | 20.10 |
| 50 | 60.4 | 30.15 |

In some instances it may be desirable to add hydrochloric acid in an amount that slightly exceeds the stoichiometric amount needed for conversion of sodium carbonate to sodium bicarbonate and in other instances it may be desirable to increase the amount of sodium carbonate.

The remaining solute constituents of the dialysate solution as prescribed by the attending physician can be added to the acid-containing solution or can be provided to the dialysate as a stream of a separate solution.

In the case of a separate solution, for example, in each liter batch thereof, 6.45 grams of dissolved calcium chloride produces a calcium level of 3 milliequivalents per liter; 1.83 grams of dissolved magnesium chloride produces a magnesium level of 1 milliequivalent per liter; and potassium chloride dissolved in amounts of 0, 2.92, 5.85 and 8.76 grams produce potassium levels of 0, 1, 2 and 3 milliequivalents per liter, respectively. Typical sodium chloride levels in such a separate solution are 149.6, 155.7 and 161.1 grams per liter batch. In combination with the sodium from the aforementioned standard sodium carbonate solution providing 40 milliequivalents of bicarbonate ion, overall sodium levels of 130, 135 and 140 milliequivalents per liter, respectively, can be obtained.

To produce a final dialysate stream of about 500 milliliters per minute to the membrane, or artificial kidney, having the constituents proportioned as described above, the diluted sodium carbonate solution is combined with the aforementioned acid-containing solution in a volumetric ratio of 34 to 1, i.e., 34 parts by volume of the diluted sodium carbonate solution to one part by volume of the acid-containing solution. In instances where the acid-containing solution also contains the prescribed additional constituents needed for proper electrolyte balance, the acid-containing solution should be added only to the diluted sodium carbonate solution because otherwise a calcium carbonate precipitate in the dialysate may be formed.

Proper proportioning of the dialysate constituents during hemodialysis can be readily monitored by a conductivity sensor because the conductivities of the diluted sodium carbonate solution and the dialysate solution are sufficiently different at 37° C. (about 6000 micromhos per centimeter and about 13,000 micromhos per centimeter, respectively) so that a failure of the dilution system for the sodium carbonate concentrate and/or the metering system for the acid-containing solution can be immediately detected and appropriate remedial measures can be implemented. It is preferred to use a pH monitor in conjunction with the conductivity sensor to insure that undiluted acid concentrate does not come in contact with the dialysis membrane.

Other illustrative concentrate compositions for in situ generation of a sodium bicarbonate dialysate are illustrated below.

To produce a dialysate having a pH of 7.2 to 7.4 and containing the constituents

| | | |
|---|---|---|
| $Na^+$ | 140 | mEq/liter |
| $HCO_3^-$ | 35 | mEq/liter |
| $Cl^-$ | 109 | mEq/liter |
| $Ca^{++}$ | 3.5 | mEq/liter |
| $Mg^{++}$ | 0.5 | mEq/liter | an aqueous acid concentrate (for 36:1 dilution) having dissolved therein

| | | |
|---|---|---|
| NaCl (mol. wt. 58.45) | 134.67 | grams/liter |
| HCl (11.6 N) | 127.7 | ml/liter |
| $CaCl_2 . 2H_2O$ (mol. wt. 147.0) | 9.26 | grams/liter |
| $MgCl_2 . 6H_2O$ (mol. wt. 203.3) | 1.83 | grams/liter | is prepared. The bacteriostatic aqueous sodium carbonate concentrate that is diluted 36-fold and combined with the foregoing acid concentrate after approximate dilution contains 169.64 grams of $Na_2CO_3.H_2O$ (mol. wt. 124.01) per liter which is equivalent to about 145 grams per liter calculated as anhydrous sodium carbonate.

The foregoing sodium carbonate concentrate can also be used at a 36-fold dilution to provide a dialysate having a pH of 7.2 to 7.4 and the following composition:

| | | |
|---|---|---|
| $Na^+$ | 140 | mEq/liter |
| $HCO_3^-$ | 35 | mEq/liter |
| $C_2H_3O_2^-$ | 5 | mEq/liter |
| $Cl^-$ | 104.5 | mEq/liter |
| $Ca^{++}$ | 3.5 | mEq/liter |
| $Mg^{++}$ | 0.5 | mEq/liter |

In the latter case, the aqueous acid concentrate, again to be diluted 36:1, has the following composition:

| | | |
|---|---|---|
| NaCl (mol. wt. 58.45) | 134.67 | grams/liter |
| HCl (11.6 N) | 112.3 | ml/liter |
| $CH_3CO_2H$ (glacial) | 10.2 | ml/liter |
| $CaCl_2 . 2H_2O$ (mol. wt. 147.0) | 9.26 | grams/liter |
| $MgCl_2 . 6H_2O$ (mol. wt. 203.3) | 1.83 | grams/liter |

The typical aqueous acid concentrate solutions suitable for the preparation of hemodialysis dialysate are illustrated hereinbelow.

| | | |
|---|---|---|
| Preparation I | | |
| NaCl | 131 | grams/liter |
| HCl (11.6 N) | 122.6 | ml/liter |
| KCl | 10.5 | grams/liter |
| dextrose | 70 | grams/liter |
| water | q.s. | |
| $Cl^-$ | 3.804 | Molar |
| $Na^+$ | 2.241 | Molar |
| $K^+$ | 0.1408 | Molar |
| dextrose | 0.3532 | Molar |
| Preparation II | | |
| NaCl | 131 | grams/liter |
| HCl (11.6 N) | 119 | ml/liter |
| KCl | 10.5 | grams/liter |
| dextrose | 70 | grams/liter |
| water | q.s. | |
| $Cl^-$ | 3.762 | Molar |
| $Na^+$ | 2.241 | Molar |
| $K^+$ | 0.1408 | Molar |
| dextrose | 0.3532 | Molar |
| Preparation III | | |
| NaCl | 159.6 | grams/liter |
| HCl (11.6 N) | 98.7 | ml/liter |
| KCl | 10.5 | grams/liter |
| dextrose | 70 | grams/liter |
| water | q.s. | |
| $Cl^-$ | 4.016 | Molar |
| $Na^+$ | 2.730 | Molar |
| $K^+$ | 0.1408 | Molar |
| dextrose | 0.3532 | Molar |
| Preparation IV | | |
| NaCl | 159.6 | grams/liter |
| HCl (11.6 N) | 93.9 | ml/liter |
| KCl | 10.5 | grams/liter |
| dextrose | 70 | grams/liter |
| $Cl^-$ | 3.961 | Molar |
| $Na^+$ | 2.730 | Molar |
| $K^+$ | 0.1408 | Molar |
| dextrose | 0.3532 | Molar |
| Preparation V | | |
| NaCl | 134.67 | grams/liter |
| HCl (11.6 N) | 127.7 | ml/liter |
| $CaCl_2$ $2H_2O$ | 9.26 | grams/liter |
| $MgCl_2$ $6H_2O$ | 1.83 | grams/liter |
| Water | q.s. | |
| $Cl^-$ | 3.857 | Molar |
| $Na^+$ | 2.304 | Molar |
| $Ca^{++}$ | 0.06299 | Molar |
| $Mg^{++}$ | 0.009001 | Molar |
| Preparation VI | | |
| NaCl | 134.67 | grams/liter |
| HCl (11.6 N) | 112.3 | ml/liter |
| $CH_3CO_2H$ (glacial) | 10.2 | ml/liter |
| $CaCl_2$ $2H_2O$ | 9.26 | grams/liter |
| $MgCl_2$ $6H_2O$ | 1.83 | grams/liter |
| $Cl^-$ | 3.679 | Molar |
| $Na^+$ | 2.304 | Molar |
| $Ca^{++}$ | 0.06299 | Molar |
| $Mg^{++}$ | 0.009001 | Molar |
| acetate group | 0.1775 | Molar |

These solutions will not support the life of microorganisms that can be potential contaminants, i.e., *Bacillus cereus, Pseudomonas stutzeri* as well as yeasts, molds, and members of Serratia and Staphylococcus. In particular, samples of concentrated sodium carbonate solutions were challenged by introducing about 1000 bacteria of a specific type and checking these samples periodically over a time period of several days. For each sample two types of control were also used. First a sample of nutrient broth was challenged with the same type and member of bacteria and periodically checked for growth to determine that the bacteria used in each instance were viable (a positive growth control). Additionally, an aliquot of each solution sample was left unchallenged but otherwise handled in the same manner as the challenged samples (a negative growth control).

Tests on aqueous solutions of sodium bicarbonate performed in the foregoing manner showed that such solutions will support the growth of yeasts, molds and Pseudomonas.

The present invention has been described with respect to the preferred embodiments, but those skilled in the art will understand that modifications and variations may be employed without departing from the essence of the invention.

We claim:

1. A sealed unit dose container containing therein an aqueous acid concentrate composition for compounding a hemodialysis dialysate which composition comprises water, dissolved solid salts and hydrochloric acid in an amount of about 93.9 milliliters/liter to about 127.7 milliliters/liter (expressed as aqueous 11.6 N HCl); the composition containing chloride ion in a concentration of about 3.5 Molar to about 4.7 Molar, sodium ion in a concentration of about 1.9 Molar to about 2.7 Molar, acetate group in a concentration of 0 Molar to about 0.525 Molar, potassium ion in a concentration of 0 Molar to about 0.14 Molar, calcium ion in a concentration of 0 Molar to about 0.125 Molar, magnesium ion in a concentration of 0 Molar to about 0.09 Molar, and dextrose in a concentration of 0 Molar to about 0.4 Molar; said composition having a pH value of about 1 to about 2.5.

2. The sealed unit dose container in accordance with claim 1 containing about 4 to about 20 liters of said aqueous acid concentrate.

3. The sealed unit dose container in accordance with claim 1 wherein the container is collapsible.

4. The sealed unit dose container in accordance with claim 1 wherein the composition contains acetate group in a concentration of about 0.15 Molar to about 0.35 Molar.

5. The sealed unit dose container in accordance with claim 1 wherein the composition contains dextrose in a concentration of about 0.2 Molar to about 0.35 Molar.

6. An aqueous acid concentrate suitable for compounding a hemodialysis dialysate which comprises water, dissolved solid salts and hydrochloric acid in an amount of about 93.9 milliliters/liter to about 127.7 milliliters/liter (expressed as aqueous 11.6 N HCl); the composition containing chloride ion in a concentration of about 3.5 Molar to about 4.7 Molar, sodium ion in a concentration of about 1.9 Molar to about 2.7 Molar, acetate group in a concentration of 0 Molar to about 0.525 Molar, potassium ion in a concentration of 0 Molar to about 0.14 Molar, calcium ion in a concentration of 0 Molar to about 1.25 Molar, magnesium ion in a concentration of 0 Molar to about 0.09 Molar, and dextrose in a concentration of 0 Molar to about 0.4 Molar; said concentrate having a pH value of about 1 to about 2.5.

7. The concentrate in accordance with claim 6 wherein the concentration of acetate group is about 0.15 Molar to about 0.35 Molar.

8. The concentrate in accordance with claim 6 wherein the concentration of dextrose is about 0.2 Molar to about 0.35 Molar.

* * * * *